United States Patent [19]
Weilandt

[11] Patent Number: 5,788,651
[45] Date of Patent: Aug. 4, 1998

[54] INSTRUMENT AND APPARATUS FOR BIOPSY

[76] Inventor: Anders Weilandt, P.O. Box 955, S-191 29 Sollentuna, Sweden

[21] Appl. No.: 783,204

[22] Filed: Jan. 14, 1997

Related U.S. Application Data

[62] Division of Ser. No. 378,402, Jan. 26, 1995, Pat. No. 5,655,542.

[51] Int. Cl.[6] .................................................... A61B 5/00
[52] U.S. Cl. .............................................................. 600/567
[58] Field of Search ............................ 128/749, 751–754; 606/167, 170

[56] References Cited

U.S. PATENT DOCUMENTS

5,156,160  10/1992  Bennett ............................. 128/754
5,188,118  2/1993  Terwilliger ......................... 128/754
5,282,476  2/1994  Terwilliger ......................... 128/754
5,535,755  7/1996  Heske ................................ 128/754

*Primary Examiner*—Max Hindenburg
*Attorney, Agent, or Firm*—Ostrolenk, Faber, Gerb & Soffen, LLP

[57] ABSTRACT

A biopsy instrument includes a tube having a finger-like projection at one end and a canula slidably disposed in the tube. After insertion of the biopsy instrument into a tissue, the tube is displaced on the canula so that the projection passes through an aperture in the canula to sever the tissue sample in the canula bore from the tissue. The projection retains the severed sample in the canula bore during withdrawal of the biopsy instrument from the tissue. A holding and control assembly having a first and second spring is provided for moving the tube and canula in a forward direction to penetrate the tissue and then substantially consecutively moving the tube in the forward direction to sever and retain the sample in the canula bore.

15 Claims, 9 Drawing Sheets

INSTRUMENT AND APPARATUS FOR BIOPSY

This is a division of application Ser. No. 08/378,402, filed Jan. 26, 1995, issued as U.S. Pat. No. 5,655,542.

BACKGROUND OF THE INVENTION

The present invention relates to a biopsy instrument and an apparatus for collecting tissue samples or the like from humans or animals, in particular by excising a segment from a tissue.

In modern medicine, biopsy, i.e., the removal of material from a living human or animal body for examination by various methods such as microscopy, is carried out on a routine basis. Typically, such a procedure is used for diagnosis of malignant and pre-malignant cell transformations, which indicate the presence of cancerous or pre-cancerous tumors.

Routine techniques in which entire tissue segments are removed for histologic examination, known as core biopsy, make use of various kinds of hollow needle-like biopsy instruments. These instruments have canulae with a sharp front edge or a notched stylet for cutting into the tissue during insertion into the selected body area. The tissue portion that is to be removed as a biopsy sample is received in the cylindrical bore of the canula. Upon withdrawal of the biopsy instrument from the body the sample is retained in the cylindrical bore by mechanical or suction means and is separated from the main tissue body during the withdrawal process. The removed samples typically have a generally oblong cylindrical shape, or a longitudinal half-cylindrical shape.

The quality, e.g., width, length and amount of crushed cells, of biopsy samples for cytologic or histologic examination is an important factor that affects the examination result. Tissue biopsy samples should mirror the structure of live tissue as closely as possible. Therefore, strains on the samples during excision, severing from the tissue, and removal from the canula should be avoided.

Other important factors are the precision with which the tissue area selected for biopsy can be targeted by the biopsy instrument, the ease with which the biopsy instrument can be manipulated, the trauma that is caused to the patient by the procedure, and the cost of the biopsy instrument.

Patient trauma is minimized by minimizing transmission of kinetic energy by means of the lowest possible friction to surrounding tissue and the smallest possible moving mass/area during the biopsy needle stroke, and by keeping the portion of the biopsy instrument that is inserted into the patient's body as small as possible for a given volume of biopsy sample. Targeting is facilitated by modern tissue imaging methods, such as by ultrasound. Ease and, thus, reproducibility of manipulation is facilitated by automatization.

U.S. Pat. No. 5,282,476 discloses an automated core biopsy device in which the canula is provided over a stylet that directs the canula to the biopsy site. After insertion, the canula is urged past the stylet to collect the sample. Suction means are employed for sample retention. However, this biopsy device is of rather complex design because of the suction means and requires substantial manipulating skills. In the hands of an untrained user, the device may yield uncertain results.

Automated core biopsy devices (ACBD) using sample retention means other than suction are known in the art. A combination of the so-called "True Cut" needle with an ACBD is disclosed in U.S. Pat. No. 4,699,154. The "True Cut" needle includes a canula with a sharp front edge and enclosing a cylindrical stylet that has a semicylindrical recessed portion near the point. Insertion of the stylet into tissue (by spring action) is followed by sliding the canula over the stylet, thus cutting and trapping a semicylindrical portion of tissue in the recessed portion of the stylet. The "True Cut" needle has a substantial drawback in that it can extract samples having half of the canula volume only, and also compromises tissue sample quality by forcing the stylet through the sample area.

Another biopsy instrument incorporating a "True Cut"-type needle is disclosed in Reissued U.S. Pat. No. Re. 34,056. One end portion of the needle assembly of this biopsy instrument is contained in a housing. Compressed springs in the housing expand to urge consecutively the needles away from the housing during the sampling of tissue.

Other needle types that use the full volume of the canula or of canula-like devices are known. For instance, U.S. Pat. Nos. 4,177,797, 4,781,202, and 4,785,826. They are, however, not suited for incorporation in an ACBD and/or have other drawbacks.

SUMMARY OF THE INVENTION

In this specification, the terms "proximal" and "distal" refer to the person extracting a biopsy sample. Thus, the proximal end of a biopsy apparatus is its rear end, pointing away from the patient.

It is an object of the invention to provide a biopsy instrument that maximizes sample volume and minimizes patient trauma during tissue extraction, and provides a sample that retains the microscopic and macroscopic properties of the tissue from which it has been taken.

It is another object of the invention to provide a biopsy apparatus that is a combination of an automated holding and control assembly and a biopsy instrument that provides the aforementioned results.

It is yet another object of the invention to provide a disposable biopsy instrument kit having the aforementioned characteristics.

It is a further object of the invention to provide an automated holding and control assembly for use with the disposable biopsy instrument kit.

It is a still further object of the invention to provide a method for harvesting tissue samples.

These and other objects of the invention are achieved by a biopsy instrument that includes a biopsy needle assembly comprising a tube with at least one finger at its distal end and a canula adapted for being slidably disposed in the tube. After the needle assembly is inserted into a tissue, the tube is displaced in a distal direction such that the finger at its distal end passes through an aperture in the canula and at least partially severs the sample in the canula bore from the tissue. The finger then retains the sample in the canula bore during withdrawal of the needle assembly from the tissue.

Another aspect of the invention provides an assembly for holding and control of the needle assembly during the tissue sample extraction. The assembly comprises first and second spring means. The tube and the canula of the needle assembly are held in the holding and control assembly and are displaced in a distal direction by operation of the first spring means. The tube is then displaced in the distal direction in respect to the canula by operation of the second spring means. The first and second spring means are operable substantially consecutively.

In a preferred embodiment, the biopsy needle assembly includes a stylet in the canula.

According to yet another aspect of the invention there is also provided a biopsy apparatus including an automated holding and control assembly. The apparatus comprises a tube with a finger at its distal end, a canula in the tube, and a stylet in the canula. The holding and control assembly comprises first and second spring means. The tube and the canula are preferably so arranged to be displaceable in a distal direction in respect to the stylet by operation of the first spring means. It is also preferred for the tube to be arranged to be displaceable in a distal direction in respect to the canula and the stylet by operation of the second spring means. Preferably, the first and second spring means are operable substantially consecutively.

According to an advantageous aspect of the invention, there is provided a disposable biopsy instrument kit comprising a needle assembly for mechanical sample retention. The needle assembly includes a canula having a lateral wall opening near its distal end and contained in a tube having a finger at its distal end that is insertable in the wall opening for retaining a tissue sample in the canula. The canula and the tube are provided, at their respective proximal end portions, with first and second heads including means for mutual releasable coupling. In a preferred embodiment, the disposable biopsy instrument kit includes a stylet in the canula.

According to yet another advantageous aspect of the invention there is provided a method for harvesting biopsy samples, which comprises injecting a biopsy instrument into tissue to a position proximal of a sample to be taken; displacing simultaneously a first part and a second part of the biopsy instrument for reception of the sample in the first part; displacing the second part to sever the sample from the tissue; retracting the biopsy instrument from the tissue; and displacing a third part of the biopsy instrument to expel the sample from the first part.

Other features and advantages of the present invention will become apparent from the following description of the invention which refers to the accompanying drawings.

DETAILED DESCRIPTION OF THE INVENTION

Figure 1:
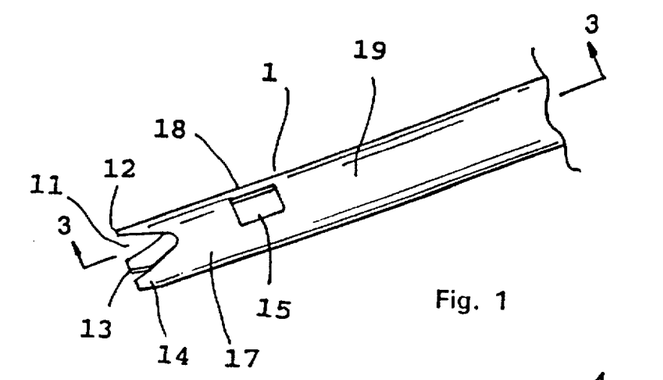
FIG. 1 is a perspective side view of the distal end portion of a canula in a first embodiment of a biopsy instrument according to the invention.
Figure 2:
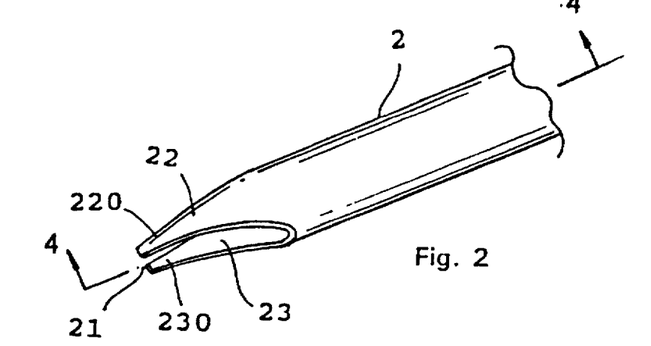
FIG. 2 is a perspective side view of the distal end portion of a finger tube of the first embodiment of the biopsy instrument.
Figures 3, 4:
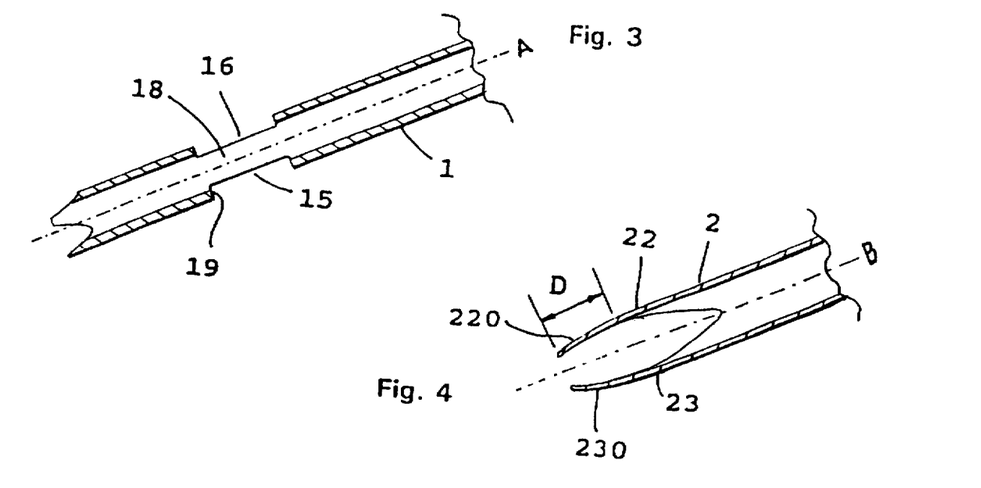
FIG. 3 is a cross-sectional view along lines 3—3 in FIG. 1.
FIG. 4 is a cross-sectional view along lines 4—4 in FIG. 2.

FIGS. 1–5 show a first embodiment of the biopsy instrument according to the invention having two substantially cylindrical tubiform elements made of, for example, stainless steel. FIGS. 1 and 3 show an inner element 1, called the canula, and FIGS. 2 and 4 show an outer element 2, called the finger tube or pincer tube. The canula 1 can slide in the pincer tube 2. In combination, the canula 1 and the pincer tube 2 form the assembly that is shown in FIGS. 5A–5F.

The distal front end of the canula 1 has a biopsy opening 11, which communicates with the canula bore. The opening 11 has an undulating or serrated edge with, for example, three teeth 12, 13, 14. At a short distance from the front edge of the opening 11 the canula 1 has two through openings 15, 16 in its lateral wall 19, hereinafter referred to as windows. The distance of each window's front edge, i.e., the edge proximate to the canula biopsy opening 11, from the proximal ends of the valleys that are formed between adjacent teeth 12, 13, 14 about equals the axial length of the windows 15, 16. Windows 15, 16 preferably are of rectangular form (disregarding the curvature of the tube wall 19) and face each other symmetrically in respect of the axis A of the canula 1.

Figure 5A:
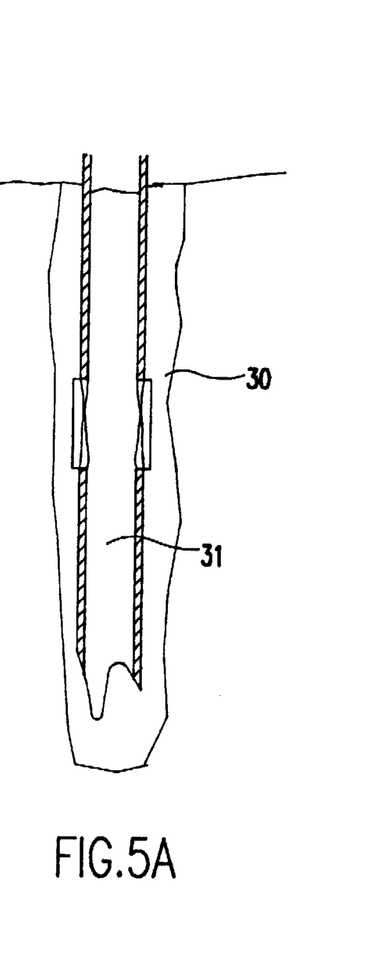
FIGS. 5A–5F shows in cross-section an assembly of the canula of FIG. 1 and the finger tube of FIG. 2 in consecutive stages of tissue sampling.
Figure 5B:
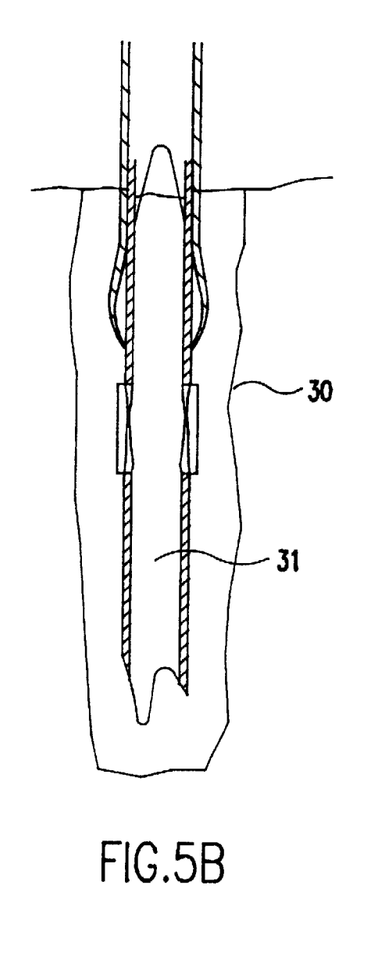

The distal front end of the pincer tube 2 has an axial front opening 21 that communicates with the bore of pincer tube 2. Two pincer-like resilient fingers 22, 23 are provided at the opening 21. Free end sections 220, 230 of the fingers 22, 23 are bent inwardly towards the axis B of the pincer tube 2 so as to make the distance between their ends in a non-restricted state somewhat less than the inner diameter of the pincer tube 2 and the outer diameter of the canula tube 1. When the pincer tube 2 is slid onto the canula 1 to form the assembly that is shown in FIGS. 5A–5F the free end sections 220, 230 abut resiliently the outside of the canula 1 (FIG. 5B). Over an axial distance D the width of the pincer fingers 22, 23 in the circumferential direction is smaller than the width of the windows 15, 16 in a circumferential direction. This width of each window 15, 16 is within a radial angle of about 90°, and the portions 17, 18 of the wall 19, which remain between the windows 15, 16, thus also are within a radial angle of about 90°.

In use, the canula 1 is inserted into a soft tissue 30 with its distal front end foremost. The canula 1 may be simultaneously rotated so that its inner bore receives a generally cylindrical piece of an excised tissue sample 31 (FIG. 5A), still connected at its base to the tissue area from which it has been excised.

The distal front end of the pincer tube 2 is then slid onto the canula 1 at the proximal canula end (not shown). The canula and pincer tube assembly 1, 2 thereby formed may have such a slid-on configuration at the start of the biopsy procedure, for instance, when used in a full biopsy apparatus that includes holding means etc., as described in further detail below. The proximal end wall of the canula 1 may be somewhat tapered at its outside to aid the sliding-on operation.

When assembled, the pincer tube 2 can be pushed forward into the tissue 30 with the canula 1 functioning as a guide. FIG. 5B shows the pincer tube 2 pushed forward into the tissue 30 along a part of the canula 1.

Figure 5C:
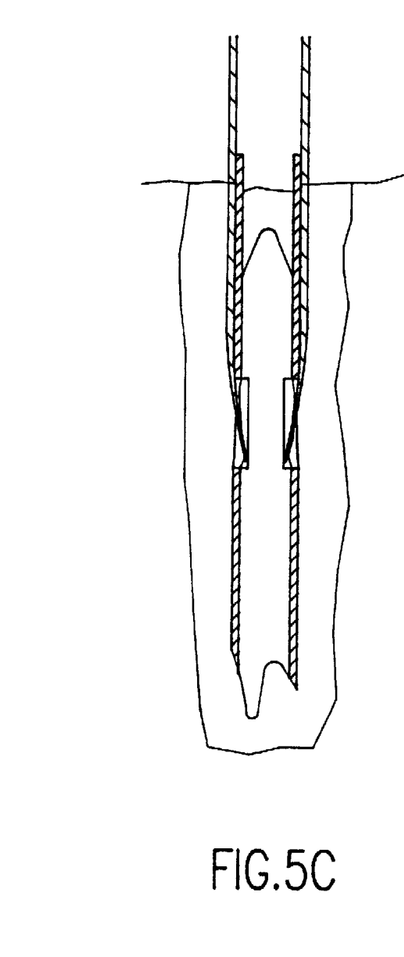

In case the pincer free end sections 220, 230 do not have the same radial orientation as the windows 15, 16 they are brought into position by slightly rotating the pincer tube 2 to make the sections 220, 230 slide into the windows 15 and 16, respectively, on further forward displacement of the pincer tube 2 (FIG. 5C). Correct orientation of the canula 1 and the pincer tube 2 can be assisted by visual or other guide marks or similar means on the canula 1 and the pincer tube 2. It is also possible to slide the pincer tube 2 along the canula 1 until the pincer end sections 220, 230 are resting on the wall portions 17, 18. Thereafter, a slight rotation of the pincer tube 2 will make the end sections 220, 230 snap into the windows 15, 16.

Figure 5D:
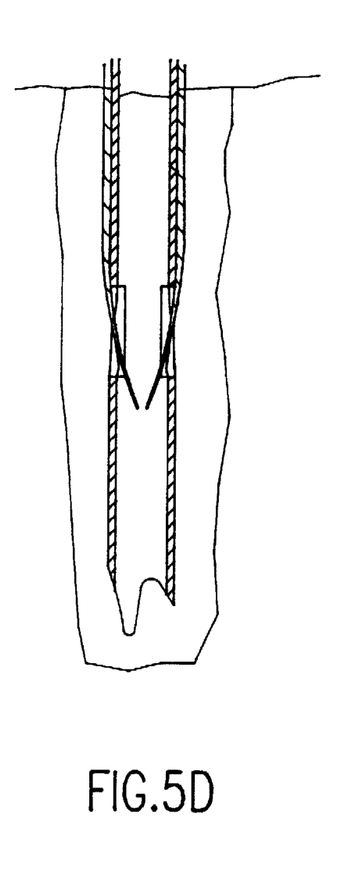

In the next step, the pincer tube 2, which is now radially locked with its end sections 220, 230 into windows 15 and 16, respectively, is further displaced forwards. Thereby, the fingers 22, 23 are deflected by the distal circumferential edges of the windows 15, 16 in a skew radial direction thereby approaching the axis A of the canula 1. In this process, the fingers 22, 23 compress and/or cut the dissected tissue segment 31 (FIG. 5D).

Figure 5E:
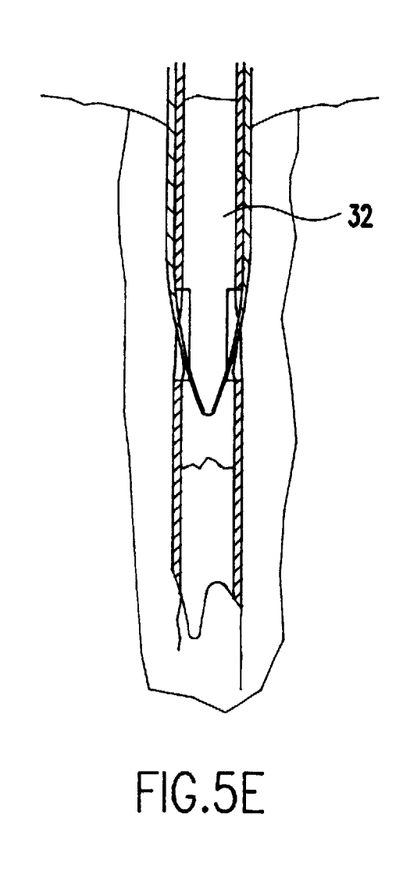
Figure 5F:
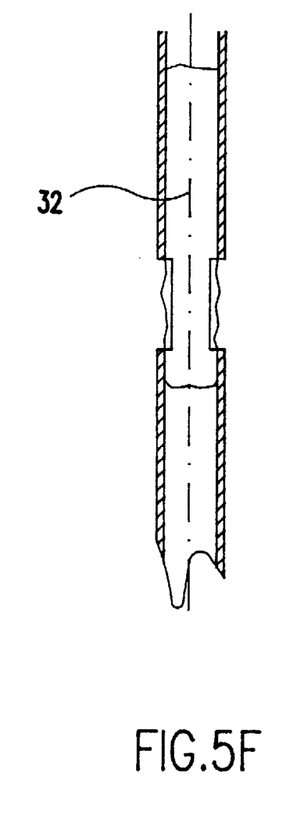

The canula 1 and the pincer tube 2 are locked in position so that mutual rotation and further distal displacement of the pincer tube 2 in respect of the canula 1 is prevented. When the assembly 1, 2 is then withdrawn from the tissue, the partially dissected tissue segment 31 is torn off (at some point between the pincer end sections 220, 230 and the base of the dissected tissue segment) and retained within the canula 1 (FIG. 5E).

Upon retraction of the assembly 1, 2, the pincer tube 2 is removed from the canula 1 by reversing the steps shown in FIGS. 5A–5D. The torn-off tissue segment, i.e., the biopsy sample 32, in the canula bore (FIG. 5F) can then be removed by means of, for instance, a cylindric rod that fits into the bore of the canula 1.

Such a cylindric rod, preferably a stylet, can be included in the assembly 1, 2 from the start. Its function corresponds to a stylet 5 in the second embodiment that is illustrated in FIGS. 6–11. The incorporation of a stylet in the assembly 1, 2 so that its tip protrudes from the canula front opening 11 allows insertion of the assembly 1, 2 into tissue to a selected depth without a sample of the tissue being retained in the assembly 1, 2. A further sampling insertion of the assembly 1, 2 can be done after retraction of the stylet in a proximal direction in respect of the canula 1 and the pincer tube 2.

FIGS. 6–11 show a second preferred embodiment of the invention, in which a biopsy instrument is retained in a holder including control means and shown in consecutive stages of biopsy sample collection. For the sake of clarity the combination of the biopsy instrument and the holder is termed biopsy apparatus.

Figures 6, 7:
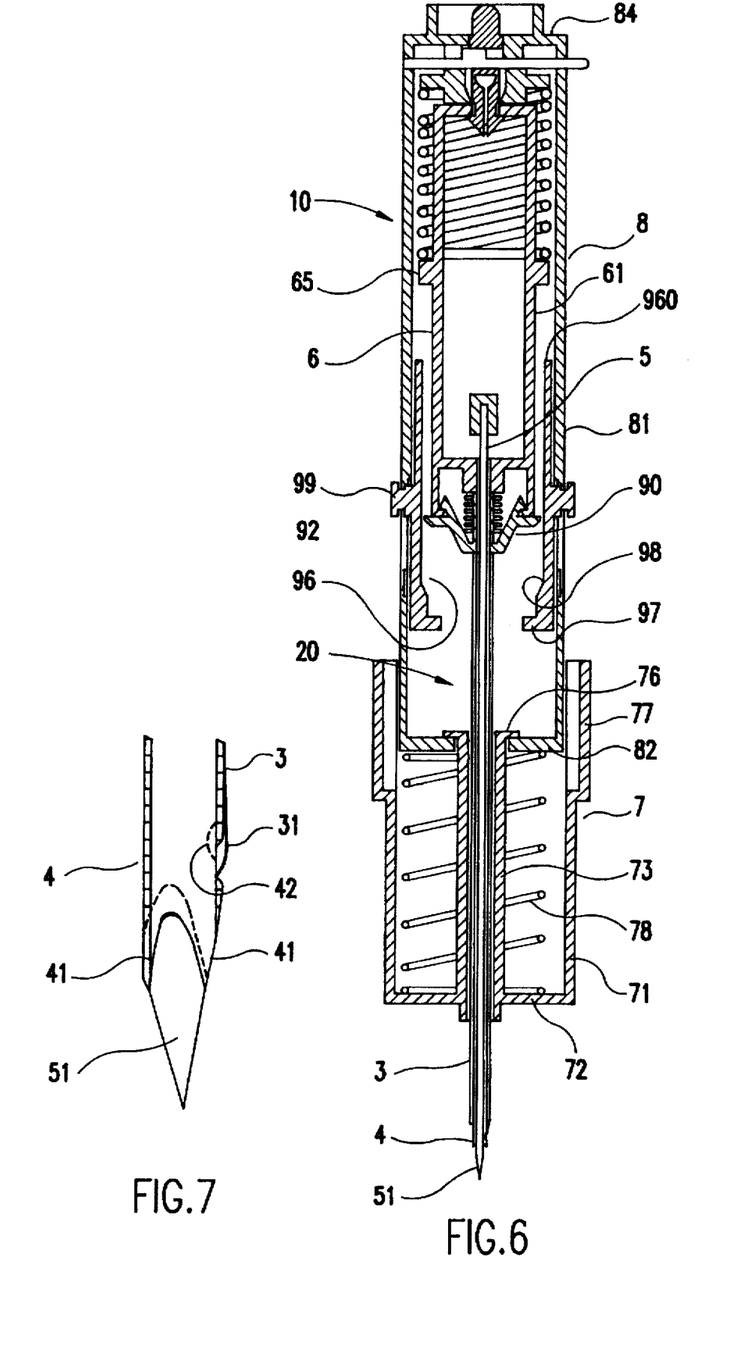
FIG. 6 is a cross-sectional view of a biopsy apparatus according to the invention in a pre-sampling stage with a second embodiment of a biopsy instrument according to the invention mounted in a holding and control assembly.
FIG. 7 is an enlarged view of the distal end portion of the biopsy instrument of FIG. 6.

FIGS. 6 and 7 show a biopsy apparatus of the second embodiment in an initial pre-sampling stage. A biopsy instrument 20 of this second embodiment has a canula 4, which is slidingly disposed in a hook finger tube 3, and a stylet 5, which is slidingly disposed in the canula 4.

As will be explained hereinafter the mutual cooperation of the canula 4 and the hook finger tube 3 of the second embodiment of the invention is similar to that of the canula 1 and the pincer tube 2 of the first preferred embodiment of the invention.

The stylet 5 is not a necessary element of the second embodiment of the invention but its inclusion is preferred. Similarly preferred is the inclusion of a corresponding stylet member (not shown) in the first embodiment of the invention.

The biopsy instrument 20 is axially mounted in a holding and control assembly 10 of generally cylindrical form. The biopsy instrument 20 may be centered in the holding and control assembly 10, but an eccentric arrangement is equally feasible.

The holding and control assembly 10 comprises a plunger 6, a finger tube actuator 90, a stroke controller 96, all mounted in a generally cylindrical holder body 8 having a front (distal) end 82 and a rear (proximal) end wall 84. The front end 82 of the holder body 8 is movably inserted into the rear (proximal) opening of an expeller body 7 of exteriorly generally cylindrical form and having a front base 72.

Figure 6A:
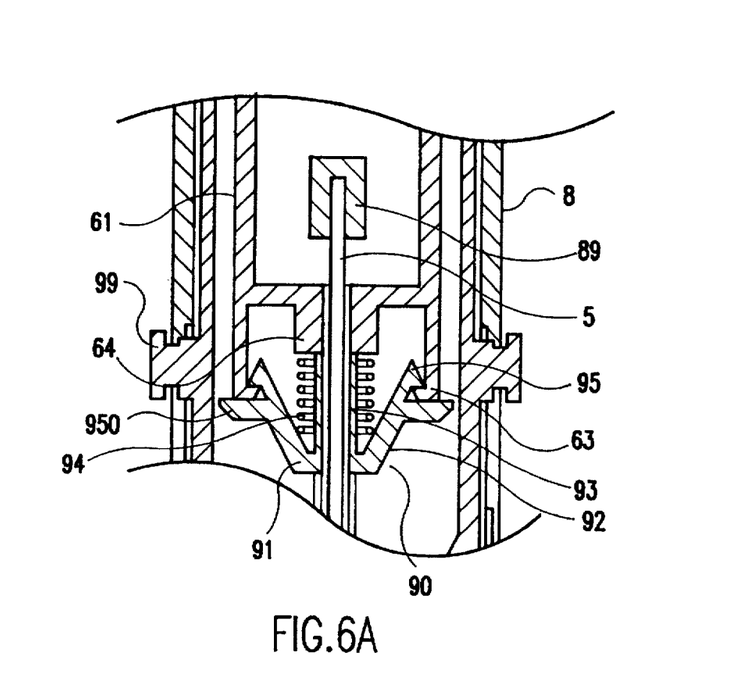
FIGS. 6A–6B are enlarged views of portions of the biopsy apparatus of FIG. 6.

As also shown in FIG. 6A, at its proximal end the stylet 5 is rigidly fixed to the holder body 8 at an extension 89 of the holder body 8. The extension 89 extends between opposing portions of the wall of the holder body 8 (in a plane that is perpendicular to the view shown in FIG. 6) through the side wall 61 of the plunger 6. To provide for the connection between the stylet 5 and the body holder 8 (via the extension 89), the side wall 61 of the plunger 6 is segmented in an axial direction at least over a segment located distally of a central plunger coil support flange 65. The stylet 5 is slidable with a flush fit in the canula 4 from the free (distal) end of which its other, sharply pointed end 51 protrudes slightly to form a needle-like tip in combination with the sharp serrated distal end 41 of the canula 4, as shown in greater detail in FIG. 7. In all states of the biopsy apparatus corresponding to the different stages of sample collection the major, axially extending central portion of the stylet 5 remains located within the bore of the canula 4.

The canula 4 is slidable with a flush fit in the finger tube 3, which has a hook finger-like free distal portion 31. In all operating states of the second embodiment, corresponding to various stages of sample collection, the major, axially extending central portion of the canula 4 remains located within the bore of the finger tube 3. As shown more clearly in FIG. 7, the hook finger 31 of the finger tube 3 is slightly withdrawn in a proximal direction from the needle-like point formed by the combined distal end portions 41, 51 of the stylet 5 and the canula 4. In this withdrawn state, the hook finger 31 is radially congruent with a portion of a notch-like opening or deflection window 42 in the wall of the canula 4 arranged near the distal end of the canula 4.

To a limited extent the plunger 6, finger tube actuator 90, and stroke controller 96 are axially displaceable within the holder body 8. This displacement varies between the different stages of sampling and is mechanically controlled to achieve the intended cooperation of the parts. The same is true of the relative movement of the holder body 8 and expeller body 7.

Figure 6B:
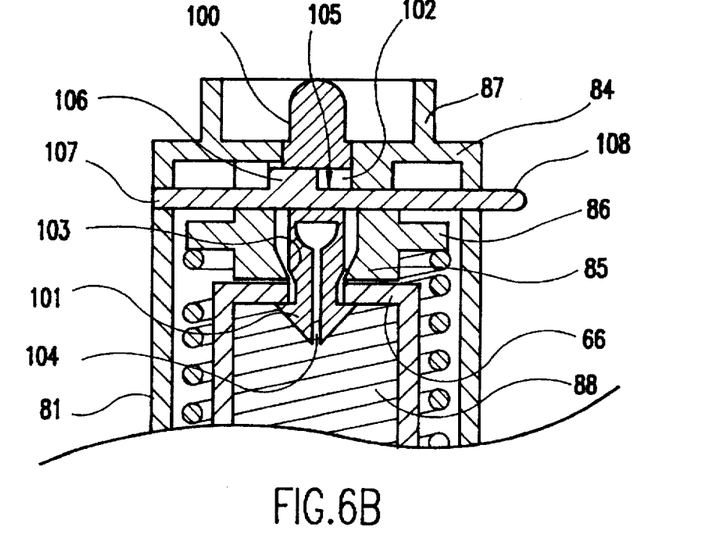

As also seen in FIG. 6B, with the proximal face of its rear wall 66, the plunger 6 abuts the front wall of a rear stop flange 86. The rear stop flange 86 extends radially from the rear wall 84 of the body holder 8 of which it forms an integral part. The plunger 6 is kept in abutment with the holder body 8 by means of a plunger release element 100. The rear stop flange 86 is generally cylindrical with a front wall portion through which a distally tapering central bore extends. Resiliently flexible pincer arms 101 of the plunger release element 100 pass through the central bore of the rear stop flange 86. The pincer arms 101 are separated by an interstice 104 that provides for their easy insertion in the central bore of the rear stop flange 86, and extend further through a corresponding bore in the rear end wall 66 of the plunger 6. In proximity of their free ends the pincer arms 101 have radially extending flange portions abutting the distal radial face of the rear end wall 66 of the plunger 6, thereby retaining the plunger 6 in abutment with the holder body 8. Proximally of their free ends provided with the flange portions the pincer arms 101 widen to an extent that would stop their further insertion into the distally tapering bore of the rear stop element 86.

The plunger release element 100 is retained in its idle (inactive) position by a locking bar 105 disposed in a radial bore 102 of the plunger release element 100. Terminal sections 107, 108 of the locking bar 105 extend radially through radial bores in the mantle wall 81 of the body holder 8. The locking bar 105 has a central portion 106 of substantially larger diameter than the terminal sections 107, 108, of which one (108) extends exteriorly of the mantle wall 81. The radial bore 102 is substantially wider in the axial direction than the terminal sections 107, 108.

The plunger 6 is retained at the holder body 8 against a force provided by a plunger steel coil 88 held in a compressed state between the proximal plunger coil support flange 86 of the body holder 8 and the central plunger coil support flange 65 of the plunger 6.

As also shown in FIG. 6A, at its proximal end the canula 4 is rigidly fixed to the plunger 6 inside a fixation socket or sleeve 64 that extends axially from the front wall of the plunger 6.

At its proximal end the finger tube 3 is rigidly fixed to a central finger tube holding sleeve 93 that is integrally formed with the finger tube actuator 90. The finger tube actuator 90 is releasably retained in abutment with a distal stop flange 63 of the plunger 6 at an actuator stop flange 950. Retention is effected by cooperation of resiliently flexible catch members 95 extending radially from the proximal end of the actuator side wall 92 which tapers in a distal direction. Catch members 95 grip the distal stop flange 63 which thus is retained between them and the actuator stop flange 950.

Retention of the finger tube actuator 90 at the plunger 6 is against a force provided by actuator steel coil 94, which is fit on the finger tube holding sleeve 93 and is held in a compressed state between the canula fixation socket 64 and the finger actuator tube front wall 91.

Set off from the finger tube actuator 90 in a distal direction is plunger stop 97 of stroke controller 96. The stroke controller 96 is disposed on or in the mantle wall 81 of the holder body 8. Independently of the other elements of the assembly 10, the stroke controller 96 can be displaced axially and set in two or more axially spaced positions for setting the stroke. A stroke control means 99 for adjusting the position of the stroke controller 96 is not described in detail and can be by screw means, catch means, snap means or other similar devices.

The expeller body 7 is mounted displaceably in the proximal direction on the holder body 8. The expeller body 7 has the general configuration of two cylinders disposed around a common central axis and extending from the common front base 72. The outer cylinder 71 has two adjoining sections of slightly differing inner diameter, a wider proximal section 77, which accommodates the aforementioned stroke control means 99, and inner cylinder 73, which limits the axial movement of the expeller body 7 by cooperation of the distal face of an outwardly drawn flange 76 at its proximal end with the proximal face of the inwardly drawn distal end flange 82 of the holder body 8. The terminal distal front portion of the wall 81 thus fits between the outer cylinder 71 and inner cylinder 73.

Insertion of the distal terminal portion of the holder body 8 into the expeller body 7 is obtained against a force trying to separate them, such as the force of an expeller steel coil 78 that is fit on the inner cylinder 73 and held in a compressed state between the terminal flange 82 and expeller base 72.

The inner cylinder 73 also functions as a finger tube guide sleeve 73. A central axial through bore of the inner cylinder 73 provides for free slidable movement of the finger guide tube 3 and, thus, of the entire biopsy instrument 20.

For an explanation of the function of the second embodiment according to the invention described above reference will now be made to FIGS. 6–11.

The biopsy instrument 20 is inserted into the soft tissues of the body in the state shown in FIGS. 6 and 7 to locate the tips of its stylet 3/canula 4/finger tube 5 proximally of the tissue area intended for sampling. During this first stage, the injection stage, the biopsy instrument 20 as well as the entire biopsy apparatus fully retain their configuration and are as shown in FIGS. 6 and 7.

Figure 8:
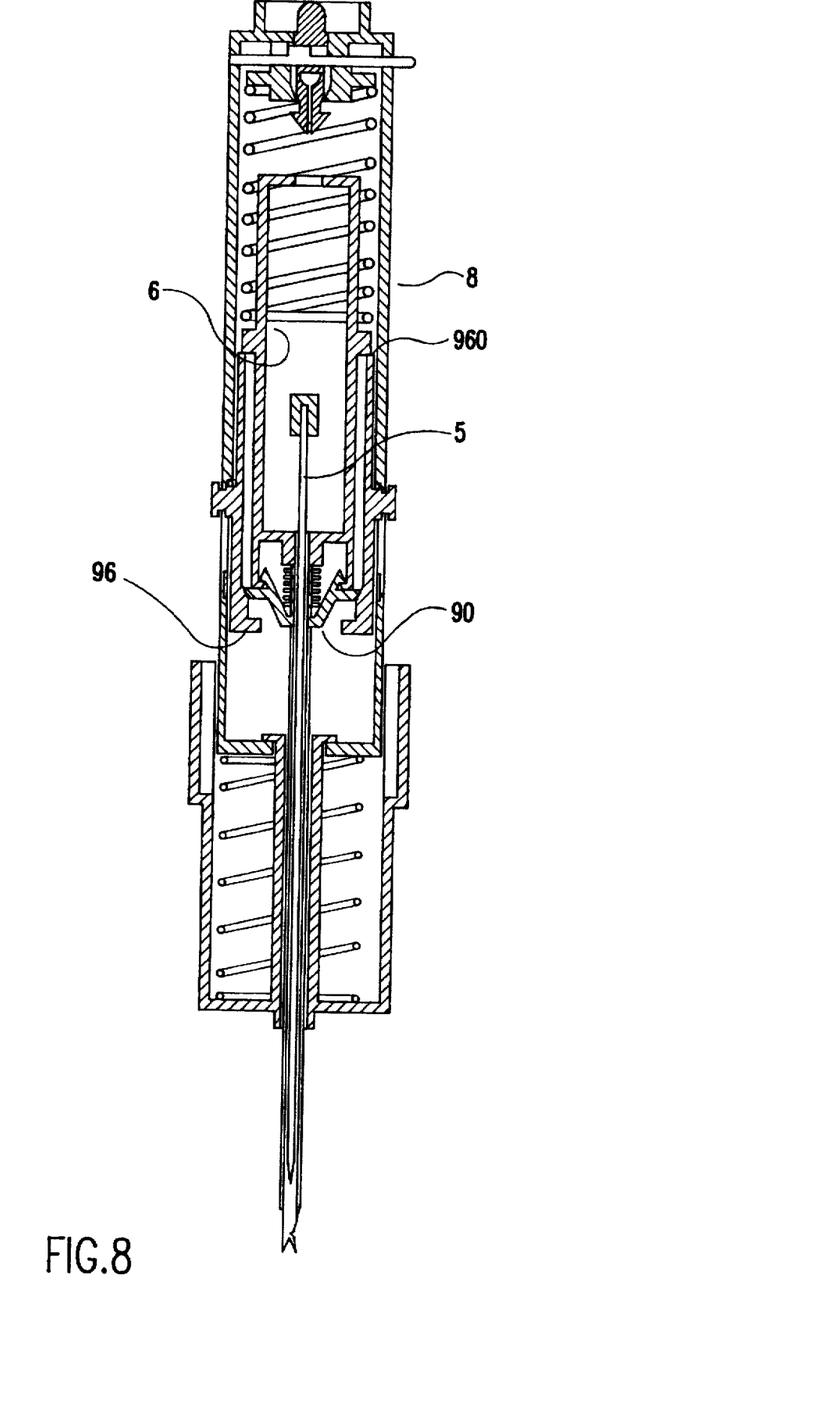
FIG. 8 shows the biopsy apparatus of FIG. 6 at the end of the sampling stage.

By pushing the terminal section 108 of the locking bar 105 protruding from the bore in the mantle 81 of the body holder 8–this can be easily done by the thumb of the hand gripping the mantle 81–the wider central portion 106 of the locking bar 105 is expelled from the bore 102 (as shown in FIG. 8). This allows axial movement of the plunger release element 100 in a distal direction over a distance defined by the difference in diameter between portions 106 and 107, 108, respectively, of the locking bar 105.

The contractive force of the plunger coil 88 displaces the locking element 100 in a distal direction. In the course of this displacement inwardly tapering shoulders 103 of the release element 100 come into abutment with the inwardly tapering wall sections of the central bore in the rear stop element 86. By applying force in a distal direction on the release element 100, its side walls abutting shoulders 103 are deflected inwardly. Such application of force can either be by selecting a plunger coil having adequate power when in a compressed state or by pressing the exteriorly protruding head of the plunger release element 100 with the thumb. This inward deflection is possible by the front end of the release element 100 being segmented by interstice 104 under formation of pincer arms 101 having radially extending support steps at their periphery holding the plunger 6. The inward displacement of the pincer arms 101 releases the plunger 6.

The substantial force of the compressed plunger coil 88 drives the plunger 6 and the abutting finger tube actuator 90 in a distal direction. The sampling elements, canula 4 and stylet 5, fixed to the plunger 6 and actuator 90, respectively, are driven into the tissue area to be sampled while preserving their relative positions. Thereby a tissue sample of length s is received in the canula 4 (see FIG. 10).

At the end of this second stage, the sampling stage, the configuration of the biopsy apparatus is that illustrated in FIG. 8. However, as will be explained below, the state shown in FIG. 8 is a dynamic state. It should also be noted that, for the sake of clarity, the radial dimensions of the biopsy instrument 20 are substantially exaggerated in the drawings.

At the end of the sampling stage the plunger 6 and canula 4 are brought to a stop by the plunger flange 65 contacting a plunger stop 960 arranged at the proximal end of the stroke controller 96. The finger tube actuator 90 and finger tube 3, however, continue their movement in a distal direction due to the finger tube actuator 90 being released from attachment to the plunger 6 by inward deflection of the actuator side wall 92 when impacting on the rounded shoulders 98 of the plunger stop 97. By this impact, catch members 95 that are integral with the actuator side wall 92 are deflected inwards and loosen their grip on the distal stop flange 63 of the plunger 6.

Figure 10:
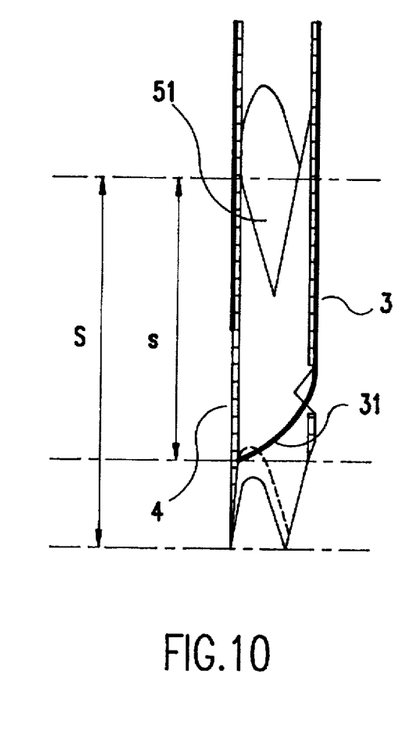
FIG. 10 is an enlarged view of the distal end portion of the biopsy instrument in the state shown in FIG. 9.

The continued movement of the hook finger tube 3 in a distal direction is due to the force exerted by the actuator coil 94. The hook finger 31, as is shown more clearly in FIG. 10, is inwardly deflected by the distal edge of the deflection window 42 and cuts through the tissue sample (not shown) contained in the canula 4 bore. The displacement of the hook finger tube 3 in this sample severing stage need only be small and the force minor in comparison with the preceding stage. The end of the severing stage is reached when the hook finger 31 has cut through most or all of the sample in an axially oblique direction and is held in this position by the residual force of the actuator coil 94.

Figure 9:
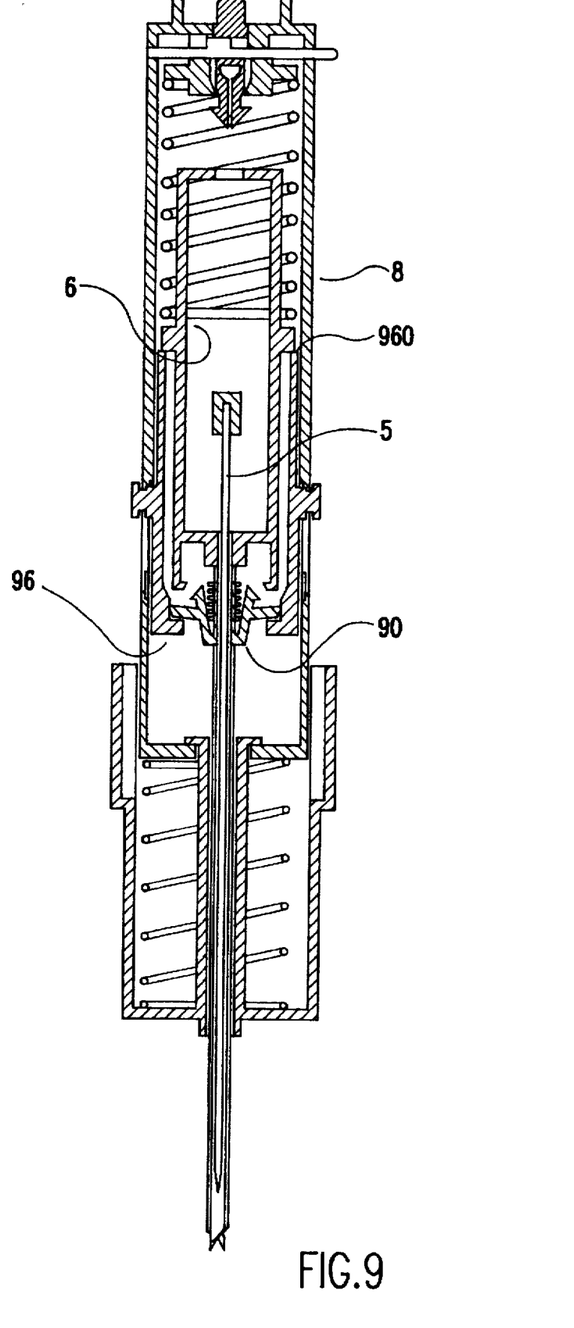
FIG. 9 shows the biopsy apparatus of FIG. 6 at the end of the sample severing stage.

The configuration of the second embodiment of the biopsy apparatus at the end of the severing stage is shown in FIGS. 9 and 10. The sample of length S contained in the canula 4 after the sampling step (an enlarged illustration at that stage corresponding to FIGS. 7 and 9 would show the canula 4 and finger tube 3 in a relative position corresponding to that in FIG. 7, and finger tube 3 and stylet 5 in a relative position corresponding to that in FIG. 9) is reduced to the length s of the severed sample after the severing step.

In the following withdrawal stage, which requires no illustration, the biopsy instrument 20 carrying the sample is withdrawn from the body.

Figure 11:
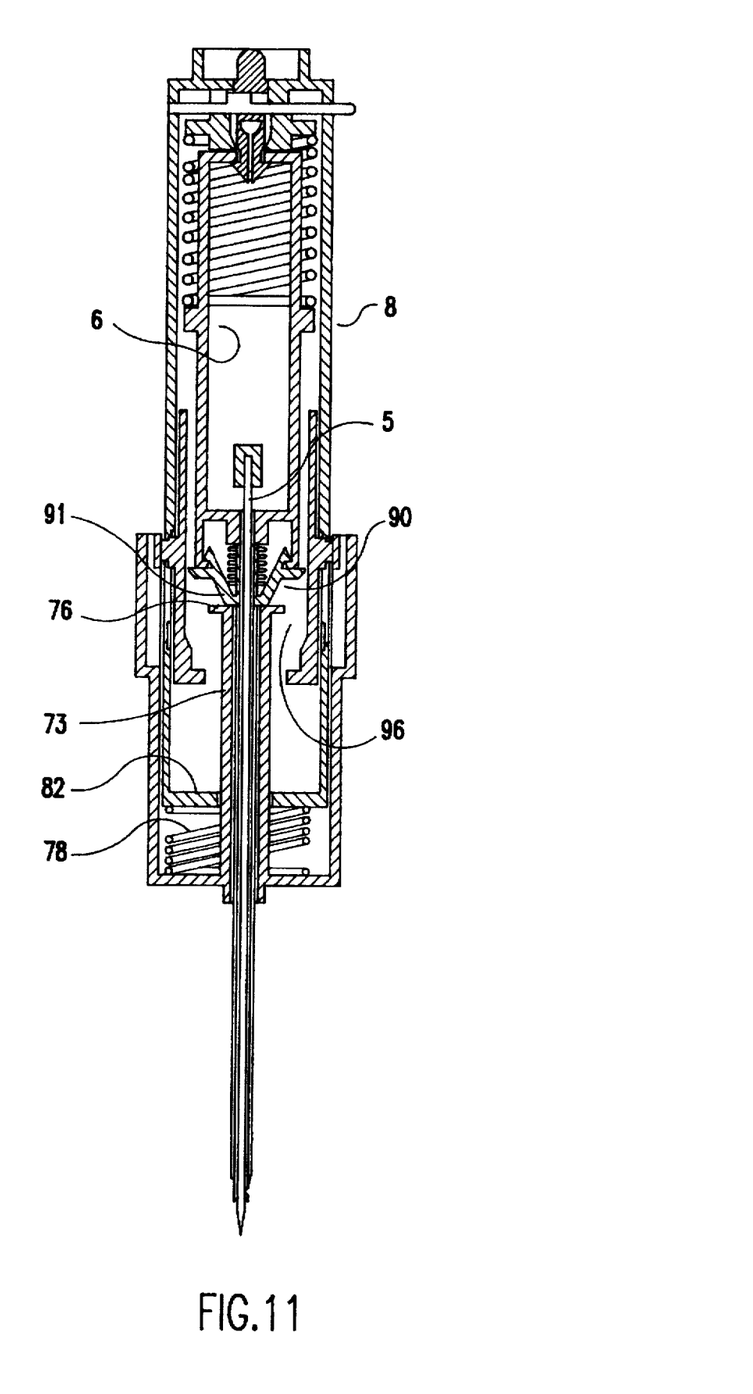
FIG. 11 shows the biopsy apparatus of FIG. 6 at the end of the sample expulsion stage.

Finally, the sample is expelled in two steps. The first step comprises movement of the hook finger tube 3 in a proximal direction in respect of the holder body 8 by, for instance, holding them one in each hand and pushing them towards each other until the actuator flange 95 snaps into the distal stop flange 63 of the plunger 6. The second step comprises movement of the expeller 7 in a proximal direction in respect of the holder body 8, by holding them one in each hand and pushing them towards each other until the sample is fully freed. FIG. 11 shows the biopsy apparatus at the end of the second expelling step.

Figure 12:
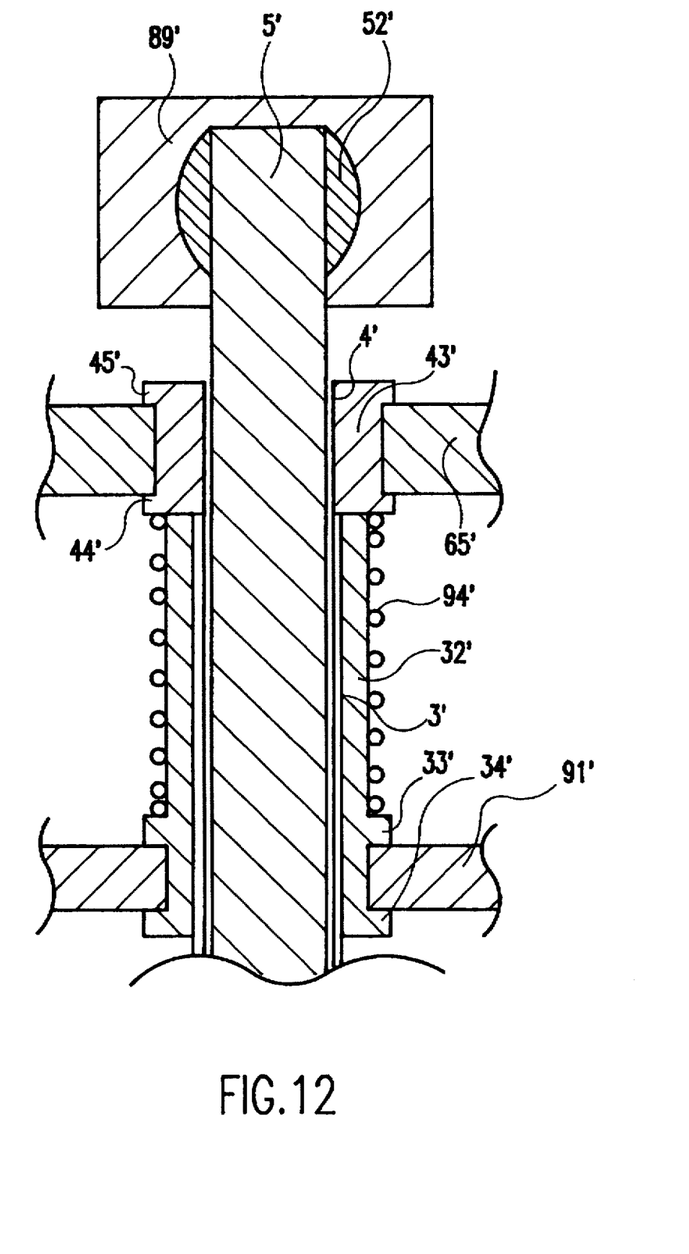
FIG. 12 shows schematically an arrangement for releasably retaining a biopsy instrument of the invention in a holding and control assembly.

FIG. 12 shows in axial cross-section an arrangement for releasably retaining a biopsy instrument of the invention in a holding and control assembly. A disposable biopsy instrument kit can be used with the arrangement shown in FIG. 12, in which a proximal end portion of the biopsy instrument is mounted in a holding and control assembly. Only the portions of the assembly that hold the various parts of the biopsy instrument kit are shown schematically in FIG. 12. The remaining portions of the biopsy instrument including its distal end portion are identical to the biopsy instrument shown in FIGS. 6–11, as are the remaining portions of the holding and control assembly.

FIG. 12 shows an annulus 52' of polymer material, for example, polypropylene, attached to the proximal end portion of a stylet 5'. The annulus 52' may be formed at the end of the stylet 5', for example, by molding. The annulus 52' may be in the shape of a circle sector toroid. The annulus 52' fits snugly into a corresponding cavity in portion 89' of the holder body 8' (not shown) and is firmly and releasably held therein. Element 89' and holder body 8' are functionally equivalent to elements 89 and 8, respectively, of the biopsy apparatus embodiment that is shown in FIGS. 6–11. Retention and removal of the proximal end portion of the stylet 5' in the element 89' can be arranged, for example, by using an element 89' which is fully or partially sectioned into two mirror halves in the plane of FIG. 12. In a mounted state of the stylet 5' in the holding and control assembly, the two mirror halves of element 89' are held together by, for instance, resilient means (not shown), which may be integrally formed with element 89'. Element 89' can also be made of resilient material, which permits the proximal end portion of the stylet 5' to be inserted from a distal direction into the cavity of the element 89'.

At its proximal end the canula 4' has a ring 43', which may be made of a polymer, such as polypropylene. The ring 43' is firmly attached to the exterior surface of the canula 4'. At its distal and proximal ends the ring 43' has peripherally extending flanges 44' and 45', respectively. The flanges 44' and 45' define between them a recess arranged for receiving a radially inwardly directed terminal portion of a radial flange 65' of plunger 6' (not shown). Retention and removal of the of flange 65' in the recess of the ring 43' can be done, for example, according to the features that are outlined above in respect to the elements 5' and 89'.

At its proximal end finger tube 3' has a sleeve 32' that is firmly attached to the exterior surface of the finger tube 3'. At its distal end the sleeve 32' has a peripheral recess defined by flanges 33, 34' and arranged for receiving a radially inwardly extending flange 91' of actuator 90' (not shown). The actuator 90' differs from the actuator 90 that is shown in FIG. 6A in that the central finger tube holding sleeve 93 of the actuator 90 is replaced with the sleeve 32'. An actuator coil 94' surrounds the sleeve 32' and rests with its distal end against the proximal end face of flange 33' and its proximal end abuts the distal face of the flange 44' of ring 43'. Since the elements 32' and 43' in a retained state of the biopsy instrument are firmly (but releasably) attached to the actuator 90' (only its flange 91' being shown) and the plunger 6' (only its flange 65' being shown), respectively, the function of the actuator coil 94' is retained and is fully equivalent to that of coil 94 (shown in FIGS. 6–11).

It is also possible to include in the disposable biopsy instrument kit other parts of the holder and control assembly for convenience of mounting and dismounting. It is thus possible—and proffered—to, for instance, include in the disposable biopsy instrument kit the actuator 90 (possibly including the coil 94) of the biopsy apparatus embodiment that is shown in FIGS. 6–11. Also other combinations that incorporate in the disposable biopsy instrument kit various parts of the holding and control assembly are feasible, and a person skilled in the art will have no difficulty in selecting those which, in regard of operation convenience or for manufacturing reasons, are advantageous.

A preferred material for the biopsy instrument is stainless steel but also other metals and non-metallic materials of which tiny tubes can be drawn may be used. The stylet, for instance could be made from a suitable polymer, such as polyacrylonitrile. The radial dimensions of the canula and the finger tube are not critical except for their mutual fit. Typical outer diameters are: canula 1.2 mm (0.047 in.); finger tube 1.6 mm (0.063 in.); stylet 0.8 mm (0.0315 in.).

A range of conventional polymer materials may be used for the various components of the holding and control assembly, such as polycarbonate, polypropylene, and acrylonitrile-butadiene-styrene (ABS) copolymers. Steel is the most preferred material for the coils but other appropriate materials can be used to releasably load the plunger and the finger tube actuator, respectively, for instance elastomers, such as natural or synthetic rubber. Such coils or other load-providing elements may be provided in a compressed state, such as in the second preferred embodiment, but they may also be provided in an extended state from which they have a tendency to contract.

A holder/control assembly design in which one or two extended load-providing elements are substituted for coils 88 and/or 94 will have to differ from the design of the second embodiment shown in FIGS. 6–11 in respect of the points of application. For example, substitution of coil 88 by an expanded resilient material, such as rubber, would suggest points of application (fixation) located at abutment face 960 and radial flange 65.

It is also possible to substitute one or both of the displacement means for the canula and/or the finger tube (coils 88, 94 in the second preferred embodiment) by other means, such as fluid power systems, magnetic means comprising permanent magnets, and electromagnetic means, such as means comprising iron-core solenoids. It is furthermore possible to substitute the (second) displacement means acting solely on the finger tube/actuator by the inertia of this combination when moving forwards. It is preferred to set the inertia of the finger tube/actuator combination by providing an actuator of adequate mass. Frictional forces acting on the finger tube during withdrawal of the biopsy instrument containing the tissue sample from tissue will retain the finger tube in its distal terminal position.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A holder for holding and controlling a biopsy instrument for extracting a segment from tissue or the like, the holder comprising:

a first part adapted for retaining a first part of the biopsy instrument;

a second part slidably disposed with respect to the first part;

a third part adapted for retaining a second part of the biopsy instrument, the third part being slidably disposed for movement in the first part;

a fourth part adapted for retaining a third part of the biopsy instrument, the fourth part being slidably disposed in the first part;

stroke control means for adjustably limiting movement of the third part in the first part; and first and second spring means associated with the third and fourth part of the holder and operable for moving the second and third part of the biopsy instrument in a distal direction.

2. The holder of claim 1, wherein:

the first part of the biopsy instrument is a stylet, the second part of the biopsy instrument is a cannula slidably disposed on the stylet and having an end with means for penetrating a tissue at the end and a wall having an opening extending through the wall, the third part is slidably disposed on the cannula and comprises excision means for separating a segment of the tissue when penetrated by the second part such that a sliding movement of the third part on the second part in one direction causes the excision means to pass through the opening in the wall of the second part thereby separating a segment of the tissue for extraction.

3. The holder of claim 1, further comprising means for releasably coupling the housing to the biopsy instrument.

4. The holder of claim 1, further comprising a stroke controlling element in the housing for adjusting an axial dimension of the housing to various lengths.

5. A holder for a biopsy instrument having a first part and a second part slidably disposed in the first part, the holder comprising:

a housing;

means for releasably coupling the housing to the biopsy instrument; and first means for consecutive displacement, initially of the first part and second part of the biopsy instrument in combination in forward axial direction in respect of the housing followed consecutively by displacement of the first part in respect of the second part and the housing in the same forward axial direction.

6. The holder of claim 5, wherein the first means for consecutive axial displacement comprise at least one coil spring in a compressed state.

7. The holder of claim 5, further comprising means for retaining a stylet in the housing.

8. The holder of claim 5, further comprising second means for consecutive displacement, initially of the first part, followed consecutively by axial displacement of the first part and second part in combination, in a direction opposite to the forward direction, for expulsion of a biopsy sample from the second part.

9. The holder of claim 8, wherein the second displacement means comprise an expeller body and compression spring means, the expeller body is disposed at a front end portion of the housing and is displaceable in the opposite direction against the resistance of the compression spring means.

10. The holder of claim 5, further comprising a stroke controlling element in the housing for adjusting an axial dimension of the housing to various lengths.

11. The holder of claim 5, wherein the first displacement means comprise mechanical means.

12. The holder of claim 11, wherein the mechanical means are selected from the group consisting of coil springs, leaf springs and elastomer components.

13. The holder of claim 5, wherein the first displacement means comprise fluid power systems.

14. The holder of claim 5, wherein the first displacement means comprise electrical means having ironcore solenoids.

15. A holder for a biopsy instrument having a first part and a second part slidably disposed in the first part, the holder comprising:

a housing;

means for releasably coupling the housing to the biopsy instrument; and first means for consecutive displacement, initially of the first part and second part of the biopsy instrument in combination in a forward axial direction in respect of the housing, followed consecutively by displacement of the first part in respect of the second part in the same forward axial direction for capturing a biopsy sample within the second part.

* * * * *